(12) United States Patent
Hübinette

(10) Patent No.: US 7,946,997 B2
(45) Date of Patent: May 24, 2011

(54) MEASUREMENT SYSTEM TO MEASURE A PHYSIOLOGICAL CONDITION IN A BODY

(75) Inventor: Ulrik Hübinette, Alunda (SE)

(73) Assignee: RADI Medical Systems AB, Uppsala (SE)

( * ) Notice: Subject to any disclaimer, the term of this patent is extended or adjusted under 35 U.S.C. 154(b) by 1133 days.

(21) Appl. No.: 11/707,278

(22) Filed: Feb. 16, 2007

(65) Prior Publication Data

US 2008/0200770 A1  Aug. 21, 2008

(51) Int. Cl.
*A61B 5/00* (2006.01)
*A61B 5/02* (2006.01)
*A61M 25/00* (2006.01)

(52) U.S. Cl. ......... 600/561; 600/486; 600/549; 600/585

(58) Field of Classification Search ............... 600/300, 600/485, 486, 549, 561, 585; 604/164.13
See application file for complete search history.

(56) References Cited

U.S. PATENT DOCUMENTS

| | | | |
|---|---|---|---|
| 5,498,261 A * | 3/1996 | Strul | 606/29 |
| 5,568,815 A | 10/1996 | Raynes et al. | |
| 5,938,624 A | 8/1999 | Akerfeldt et al. | |
| 6,167,763 B1 | 1/2001 | Tenerz et al. | |
| 6,428,336 B1 | 8/2002 | Akerfeldt et al. | |
| 6,565,514 B2 | 5/2003 | Svanerudh et al. | |
| 6,615,067 B2 | 9/2003 | Hoek et al. | |
| 6,618,603 B2 * | 9/2003 | Varalli et al. | 600/345 |
| 2001/0021799 A1 | 9/2001 | Ohlsson | |
| 2002/0173724 A1 | 11/2002 | Dorando et al. | |

FOREIGN PATENT DOCUMENTS

| | | |
|---|---|---|
| EP | 0 712 603 A2 | 5/1996 |
| EP | 1 616 521 B1 | 11/2007 |
| WO | WO 98/42253 A1 | 10/1998 |
| WO | WO 01/18835 A1 | 3/2001 |

* cited by examiner

*Primary Examiner* — Max Hindenburg
*Assistant Examiner* — Jonathan M Foreman
(74) *Attorney, Agent, or Firm* — Foley & Lardner LLP

(57) ABSTRACT

Measurement system comprising a sensor wire provided, at its distal end, with a physiological condition sensor to measure a physiological condition inside a patient, and to provide measured data to an external device, the measurement system comprises a transceiver unit adapted to be connected to the proximal end of the sensor wire, and a communication unit arranged in connection with the external device. The transceiver unit is adapted to communicate, by a communication signal, with the communication unit, in order to transfer measured data to the external device. The communication signal, including the measured data, is generated by the transceiver unit and transferred as an output signal and the communication unit is arranged to be connected to a standard input/output connector of the external device and to communicate with the external device in accordance with an established standard, or in accordance with relevant parts of an established standard, e.g. BP22 or USB. The measurement system further comprises a physical optical communication link arranged between the transceiver unit and the communication unit, wherein the communication signal is an optical signal transferred by the optical communication link. The transceiver unit also comprises an energy means adapted to energize the sensor, the transceiver unit and also the optical communication link.

26 Claims, 3 Drawing Sheets

MEASUREMENT SYSTEM TO MEASURE A PHYSIOLOGICAL CONDITION IN A BODY

FIELD OF THE INVENTION

The present invention relates to a measurement system comprising a transceiver unit and a communication unit for measuring a physiological condition in a body of a patient, according to the preamble of the independent claim.

BACKGROUND OF THE INVENTION

In many medical procedures, medical personnel need to monitor various physiological conditions that are present within a body cavity of a patient. These physiological conditions are typically physical in nature—such as pressure, temperature, rate-of-fluid flow—and provide the physician or medical technician with critical information as to the status of a patient's condition. Obviously, the manner by which these types of parameters are measured and monitored must be safe, accurate and reliable.

One device that is widely used to monitor such conditions is the blood pressure transducer. A blood pressure transducer senses the magnitude of a patient's blood pressure, and converts it into a representative electrical signal. This electrical signal is then supplied to a patient monitor that displays, records or otherwise monitors the magnitude of the patient's blood pressure.

Traditionally, a blood pressure transducer has consisted of a pressure responsive diaphragm that is mechanically coupled to piezoresistive elements connected in a Wheatstone Bridge-type circuit arrangement. When the diaphragm is placed in fluid communication with a body cavity (such as within the arterial or venous system), pressure induced deflections of the diaphragm cause the resistive elements to be stretched (or compressed, depending on their orientation). According to well-known principles, this alters the resistance of the elements in a manner that is proportional to the applied pressure. The magnitude of the applied pressure can thus be detected by applying an excitation power signal (usually in the form of a voltage) to the inputs of the Wheatstone bridge circuit, and by simultaneously monitoring the bridge output signal. The magnitude of that signal reflects the amount by which the bridge resistance has changed, according to Ohm's law.

Typically, an electrical cable connects the Wheatstone bridge portion of the transducer sensor to a transducer amplifier circuit contained within the patient monitor. This amplifier circuit supplies the excitation power signal to the Wheatstone bridge, and simultaneously monitors the bridge output signal. The excitation power signal is typically in the form of a voltage and, depending on the monitor type and manufacturer, can have varying magnitudes and formats, both time-varying (sinusoidal, square-waved and pulsed) and time independent (DC).

According to the principles under which conventional Wheatstone bridge transducers operate, transducer amplifier circuits in most patient monitors have been designed to expect a sensor output signal having a magnitude that is proportional to the magnitude of the excitation power signal and also proportional to the magnitude of the sensed pressure. Because different monitors supply excitation power signals having different magnitudes and/or frequencies, standard proportionality constants have been developed. These proportionality standards allow any sensor to be readily adapted for use with any patient monitor also calibrated to adhere to the proportionality standard.

Several benefits are provided by this compatibility. Blood pressure transducers could be used interchangeably with patient monitors from different manufacturers. As such, medical personnel were not required to select a specific transducer for use with a specific monitor. Further, hospital investments in pre-existing patient monitors were preserved, thereby reducing costs. As a consequence, vital signs monitors adhering to these proportionality standards have achieved almost universal acceptance in medical environments.

However, the blood pressure transducers and monitors that have been previously used, and the resulting standards that have evolved, are not without drawbacks. For instance, the sensors used in these systems were typically positioned external to the patient's body and placed in fluid communication with the body cavity via a fluid-filled catheter line. Pressure variations within the body cavity are then indirectly communicated to the diaphragm by way of fluid contained with the catheter line. As such, the accuracy of such systems has suffered due to variations in hydrostatic pressure and other inconsistencies associated with the fluid column.

In response to this problem, miniaturized sensors using advanced semiconductor technologies have been developed. These types of transducer sensors are extremely accurate, inexpensive and still utilize the well known Wheatstone bridge-type of circuit arrangement, which typically, at least partly, is fabricated directly on a silicone diaphragm. Further, the sensors are sufficiently small such that they can actually be placed on the tip of an insertable guide wire, or catheter, and reside directly within the arteries, tissues or organs of the patient. This eliminates the need for a fluid line because the fluid pressure is communicated directly to the transducer diaphragm. As a result, these sensors—often referred to as guide wire-tipped, or catheter-tipped, transducers—provide a much more accurate measurement of the patient's blood pressure.

Unfortunately, the electrical configurations of these miniaturized semiconductor sensors are not always compatible with the transducer amplifiers in existing patient monitors. For instance, the miniaturized sensors often cannot operate over the entire range of excitation signal magnitudes and frequencies found among the various types of patient monitors. Thus, they cannot be connected directly to many of the patient monitors already in use. To be used with such existing monitors, a specialized interface must be placed between the sensor and the monitor. Such an arrangement necessitates additional circuitry on the interface and, because existing monitors have been designed to provide only limited amounts of power, the additional circuitry may require an independent source of electrical power. As a consequence, use of the newer miniaturized sensors often adds cost and complexity to the overall system.

In addition, because of the above limitations, these sensors must often be configured to generate an output signal which is proportional to the pressure sensed, but that is not related to the excitation signal, supplied to the sensor by the monitor, in a way that is directly usable by the physiology monitor, e.g. the sensitivity may be different. As discussed, this does not conform to the electrical format required by the many monitors that are commercially available and already in widespread use. As such, the newer sensors can only be used with specific monitor types, thereby requiring additional, and often redundant, equipment to be purchased. This is especially undesirable given the cost sensitivities so prevalent in today's health care environment.

The Association for the Advancement of Medical Instrumentation ("AAMI") has defined power requirements for physiology monitors and in particular the input/output connector to a sensor wire assembly must comply with the standard set by American National Standards Institute ("ANSI")/AAMI BP22-1994 (referred to as "BP22" in the following).

According to the BP22-standard an input/output connector arranged at the proximal end of a five line connector cable includes a pair of differential output signal lines. The output signal lines are driven by a sensor adapting circuitry's output digital to analog converters. The differential output signal, by way of example, operates at 5 $\mu V/mmHg/V_{EXC}$. An operation range of $-150$ $\mu V/V$ to $1650$ $\mu AV/V$ therefore represents a sensed pressure range of $-30$ to $330$ mmHg. An exemplary resolution (minimum step) for the differential output signal is 0.2 mmHg.

U.S. Pat. No. 5,568,815 discloses an interface circuit for interfacing a sensor to a patient monitor. The interface circuit includes a power supply circuit that receives an excitation power signal generated by the patient monitor, and derives therefrom unregulated and regulated supply voltages for use by the electrical components on the interface circuit. Further, the power supply circuit generates an appropriate sensor excitation signal. The interface circuit further includes receiving circuitry for receiving a sensor output signal generated by the sensor. A scaling circuit then scales that signal into a parameter signal that is proportional to the physiological condition detected by the sensor, and that is also proportional to the excitation power signal generated by the patient monitor.

An obvious drawback of the device of U.S. Pat. No. 5,568,815 is that, in order to connect the sensor to the monitor, a separate additional unit in the form of the interface circuit is required.

Furthermore, in U.S. Pat. No. 5,568,815 is also discussed the issues of having an electrically conducted device such as a pressure transducer connected both to a patient and to an electronic monitoring instrument. Great care must then be taken to insure that electrical currents at standard power line frequencies cannot flow from the patient, through the transducer connection, and to ground. An additional risk occurs in patents which are undergoing defibrillation while having an electrically conductive transducer attached.

In the above-referenced US-patent it is suggested to include opto-isolators to address the insulation problem in order to achieve the transfer of measurement data to the monitor device. The energy used by the sensor is transferred from the monitor side to the sensor e.g. with a DC/DC connection.

The general object of the present invention is to achieve an improved device being smaller and lighter and more user-friendly than the presently available systems, and also being even safer than today's systems when used in connection when a defibrillation procedure is performed.

SUMMARY OF THE INVENTION

The above-mentioned object is achieved by the present invention according to the independent claim.

Preferred embodiments are set forth in the dependent claims.

In particular the present invention obviates the need of a physical galvanic connection between the patient and the monitoring device by arranging a physical optical link connection between an easy-to-use transceiver unit and a communication unit, and in particular that the measured pressure data is received by the transceiver unit where it preferably is processed and then transferred to the communication unit as a output signal. The transceiver unit, when receiving sensor data from the sensor, is adapted to self-contained, directly or at a later time, generate an optical transmission of data to the communication unit. The transceiver unit is provided with an energy means adapted to energize the sensor, the transceiver unit and also the optical communication link, thereby obviating any energy transfer from the communication unit to the transceiver unit. Thus, the optical communication link ensures that the transceiver unit is completely galvanically isolated from the communication unit.

The communication unit is adapted to be connected to an external device by a standard input/output connector in accordance with an established standard or in accordance with relevant parts of an established standard, e.g. BP22 or USB, as briefly discussed in the background section.

One presumption for equipment used for in-vivo measurements is that it safely can be used in a patient during external defibrillation and that the external device (e.g. the monitor) is protected against defibrillation shocks. Thus, if a defibrillation shock is generated by an external defibrillator and the patient has a guide wire inside the body, e.g. inside the heart, the guide wire is electrically insulated from the external monitor (equipment).

Furthermore, a major advantage of the present invention is that no user input is required in order to use the system, instead it is ready to plug-in and directly use and that the sensor signal adapting circuitry then automatically adapts the output to the applied sensor signal.

SHORT DESCRIPTION OF THE APPENDED DRAWINGS

Preferred embodiments of the present invention will be described in detail in the following with reference made to accompanying drawings, in which:

FIG. 1 shows an exemplifying sensor mounted on a guide wire in accordance with prior art and which is applicable herein.

FIG. 2 schematically illustrates a measurement system according to the present invention.

DETAILED DESCRIPTION OF PREFERRED EMBODIMENTS OF THE INVENTION

In the prior art, it is known to mount a sensor on a guide wire and to position the sensor via the guide wire in a blood vessel in a living body to detect a physical parameter, such as pressure or temperature. The sensor includes elements that are directly or indirectly sensitive to the parameter. Numerous patents describing different types of sensors for measuring physiological parameters are owned by the applicant of the present patent application. For example, temperature could be measured by observing the resistance of a conductor having temperature sensitive resistance as described in U.S. Pat. No. 6,615,067. Another exemplifying sensor may be found in U.S. Pat. No. 6,167,763, in which blood flow exerts pressure on the sensor which delivers a signal representative of the exerted pressure.

In order to power the sensor and to communicate signals representing the measured physiological variable to an external physiology monitor, one or more cables or leads for transmitting the signals are connected to the sensor, and are routed along the guide wire to be passed out from the vessel to the external physiology monitor, conventionally via physical cables. In addition, the guide wire is typically provided with a central metal wire (core wire) serving as a support for the sensor and (optionally) also as an electrical connection to the sensor, and a surrounding tubing. Hence, a sensor guide wire typically comprises a core wire, leads and a protective tubing.

Figure 1:
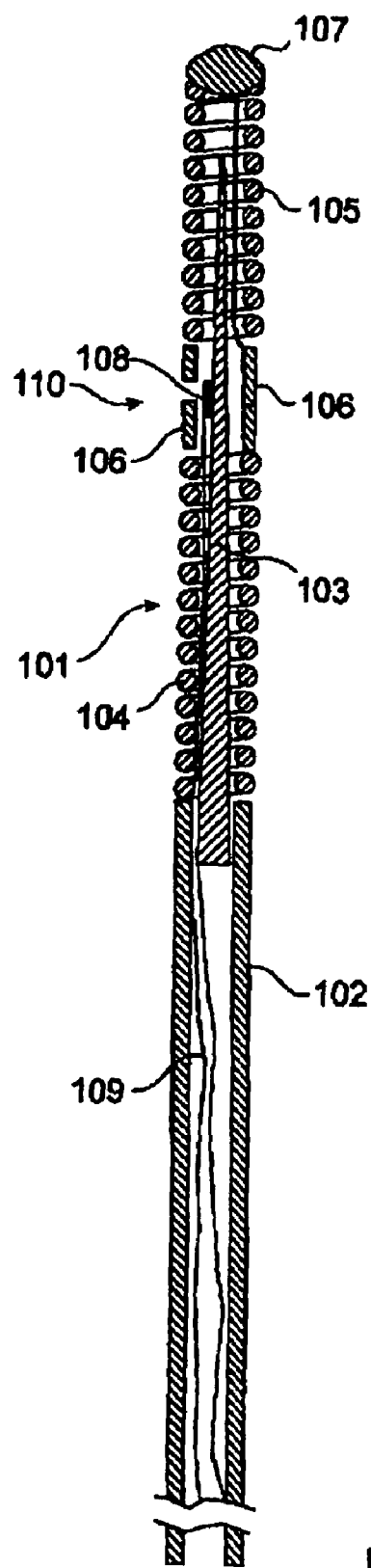

FIG. 1 shows an exemplifying sensor mounted on a guide wire in accordance with conventional design which is applicable for the present invention. The sensor guide wire 101 comprises a hollow tube 102, a core wire 103, a first spiral portion 104, a second spiral portion 105, a jacket or sleeve 106, a dome-shaped tip 107, a sensor element or chip 108, and one or several electrical leads 109. The tube 102 has typically been treated to give the sensor guide construction a smooth outer surface with low friction. The proximal end of the first spiral portion 104 is attached to the distal end of the hollow tube 102, while the distal end of the first spiral portion 104 is attached to the proximal end of the jacket 106. The proximal end of the second spiral portion 105 is connected to the distal end of the jacket 106, and the dome-shaped tip 107 is attached to the distal end of the second spiral portion 105. The core wire 103 is at least partly disposed inside the hollow tube 102 such that the distal portion of the core wire 103 extends out of the hollow tube 102 and into the second spiral portion 105. The sensor element 108 is mounted on the core wire 103 at the position of the jacket 106, and is connected to an external physiology monitor (not shown in the FIG. 1) via the electrical leads 109. The sensor element 108 comprises a pressure sensitive device in the form of a membrane (not shown in the FIG. 1), which through an aperture 110 in the jacket 106 is in contact with a medium, such as blood, surrounding the distal portion of the sensor guide wire 101.

Figure 2:
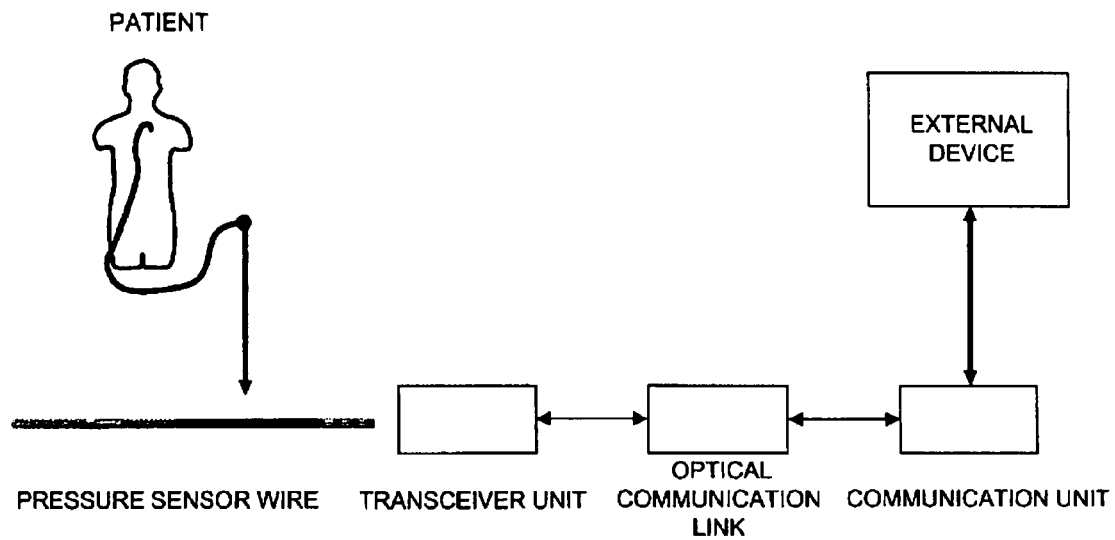

FIG. 2 is a schematic overview illustrating the application of the present invention. The measurement system according to the present invention comprises a sensor wire with a sensor to measure a physiological condition, e.g. pressure, inside a patient, and to provide measured data to an external device. The sensor wire is adapted to be connected, at its proximal end, to a transceiver unit adapted to optically communicate via an optical signal with a communication unit arranged in connection with an external device (also referred to as external physiology monitor), in order to transfer measured data to the external device.

The external device may be a dedicated device, i.e. a patient monitoring device, preferably provided with a monitor, or a PC provided with relevant software and external connections to receive and to process the measured data from the measurement system. One example of a dedicated device applicable herein is disclosed in U.S. Pat. No. 6,565,514.

Figure 3:
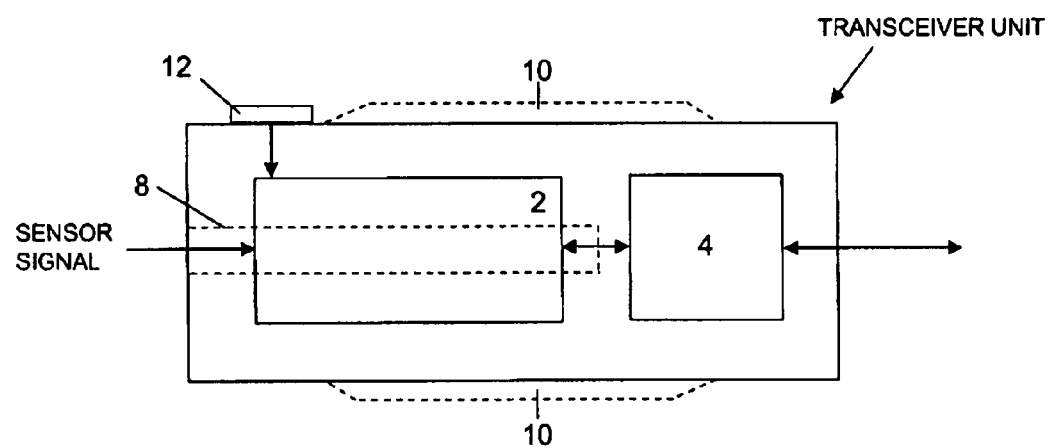
FIG. 3 shows a block diagram schematically illustrating a transceiver unit according to a preferred embodiment of the present invention.

FIG. 3 shows a block diagram schematically illustrating the transceiver unit according to the present invention. As shown in FIG. 2 the transceiver unit is adapted to be connected to the proximal end of a sensor wire provided, at its distal end, with a sensor to measure a physiological condition, e.g. pressure, inside a patient. Preferably, the transceiver unit comprises a sensor signal adapting circuitry 2, which will be described in greater detail below, a communication module 4, connected to the adapting circuitry 2, that will handle the communication with the communication unit.

Both one-way and both-way communication may be used.

The measured data is independently generated by the transceiver unit and transferred as an output signal to the communication unit in a prescribed format, to be further discussed below.

The output signal is preferably in a digital form, i.e. as data packets, where the data is encoded such that the measured values are retrievable to be available and presented by the external device.

As an alternative the transmission may be an analogue data transmission.

The sensor wire is adapted to be inserted into an elongated aperture 8 of the transceiver unit. The aperture is at its inner surface provided with a number of electrical connecting surfaces (not shown) to be connected to electrode surfaces at the proximal end of the sensor wire when inserted into the aperture 8. The transceiver unit is further provided with wire fastening means (not shown) to firmly fixate the wire when correctly inserted into the aperture.

According to a preferred embodiment the transceiver unit is adapted to receive the proximal end to the sensor wire having an outer diameter of 0.35 mm, i.e. the inner diameter of the elongated aperture 8 must be slightly larger than 0.35 mm.

U.S. Pat. No. 5,938,624 relates to a male connector with a continuous surface for a guide wire which preferably is applied as male connector for the proximal end of the sensor wire to be connected to a transceiver unit according to the present invention. The male connector includes a core wire, and conductive members spaced apart longitudinally along the core wire. A continuous insulating material is disposed between the guide wire and the conductive members and the insulating material having an outer surface coextensive with outer surfaces of the conductive members.

As mentioned above, the transceiver unit according to the present invention is provided with a fastening means to fasten the proximal end of the wire to the transceiver unit. The fastening means may be a female connector of the type disclosed in U.S. Pat. No. 6,428,336 into which a male connector of the kind described above may be inserted and secured to provide electrical contact with contact surfaces of the male connector. The female connector comprises an insulating hollow housing containing three hollow contact members to make contact with the conductive members of the male connector. At the distal end of the female connector the fastening means for securing the male connector in the female connector are provided.

The male connector of the sensor wire used in respect of the present invention is preferably compatible with the female connector disclosed in U.S. Pat. No. 6,428,336.

When the sensor wire is fixated to the transceiver unit the unit may be used as a "handle" when guiding the sensor wire during insertion into a patient. Preferably the transceiver unit is provided with guiding means 10, e.g. in the form of one or many elongated ribs on the outer surface of the transceiver unit, or by providing the transceiver unit with a roughened surface.

The sensor wire may be fixated to the transceiver unit such that as the transceiver unit is rotated along its longitudinal axis the sensor wire is also rotated, which often is necessary in order to guide the sensor wire during the insertion procedure. As an alternative, the sensor wire is fixated to the transceiver unit in such way that the sensor wire may be rotated in relation to the transceiver unit. The rotation of the sensor wire is then achieved by firmly holding the transceiver unit by one hand and by rotating the sensor wire by the other hand.

The transceiver unit is preferably activated and initiated via an activation button 12 arranged at the housing of the unit. The activation button is preferably mechanically activated.

According to another embodiment the transceiver unit is activated and initiated when the proximal end to the sensor wire is correctly inserted into the unit. This may e.g. be achieved by arranging a push button at the bottom of the cavity into which the wire is inserted.

According to another embodiment the transceiver unit is activated and initiated when electrical connections are established between corresponding electrical contact surfaces of the female and male connectors, respectively.

According to still another embodiment the transceiver unit is activated and initiated by a remote signal generated from the communication unit in response of a command from the monitoring device.

The transceiver unit comprises energy means to energize the transceiver unit, the circuitry of the connected sensor wire and the optical communication link, more precisely the distal part of the optical communication link. The energy means is preferably a battery or a capacitor that e.g. may be included in the sensor signal adapting circuitry.

The sensor wire as well as the transceiver unit are preferably disposable units that must be able to sterilise prior use.

Figure 4:
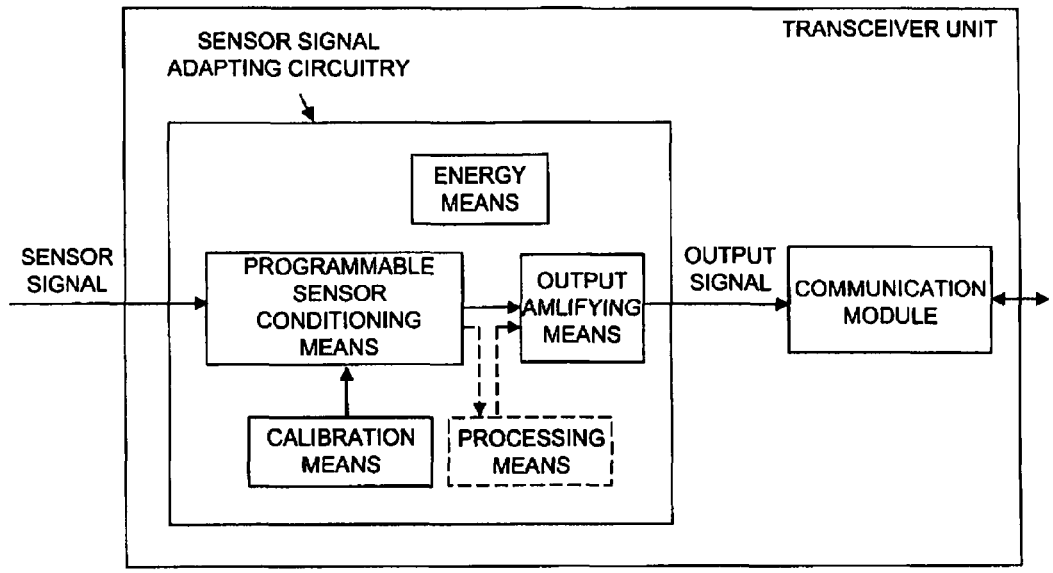
FIG. 4 shows a block diagram schematically illustrating a transceiver unit including a sensor signal adapting circuitry according a preferred embodiment of the present invention.
Figure 5:
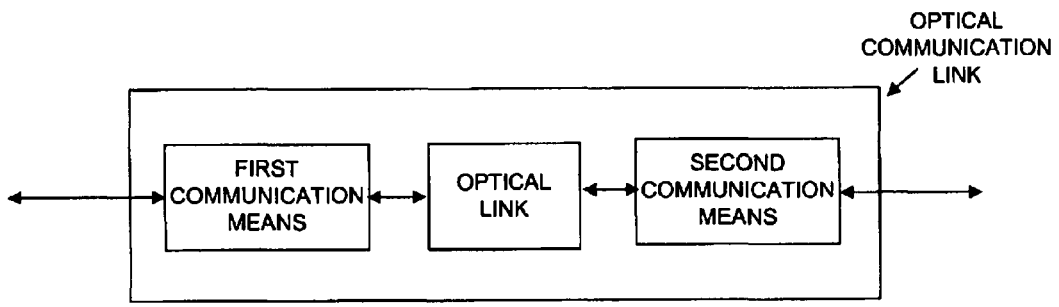
FIG. 5 shows a block diagram schematically illustrating the optical communication link according to the present invention.

FIG. 4 shows a block diagram schematically illustrating the transceiver unit according to the present invention.

With references to FIGS. 1 and 2 the sensor wire comprises a sensor element for measuring the variable and to generate a sensor signal in response of said variable, a guide wire having said sensor element at its distal portion, preferably close to its distal end, and adapted to be inserted into the body in order to position the sensor element within the body. The transceiver unit comprises the sensor signal adapting circuitry (FIG. 4), wherein the sensor signal is applied to the adapting circuitry that is adapted to generate an output signal, related to the sensor signal, in a format such that the measured variable is retrievable by an external device. According to a preferred embodiment the sensor signal adapting circuitry comprises a programmable sensor conditioning means, a calibration means, being a storage means into which calibration data may be supplied, stored and altered, e.g. an electrically erasable programmable read-only memory (EEPROM), energy means and an output amplifying means.

The programmable sensor conditioning means is preferably a PGA309 programmable analog sensor conditioner (available from Texas Instruments Inc.) specifically designed for bridge sensors.

According to a preferred embodiment of the present invention the external device supplies the sensor signal adapting circuitry with a reference voltage value optically via the optical connector link and the corresponding voltage is applied from the energy means in the transceiver unit. By considering the signal standard with which the external device complies, which is indicated to the adapting circuitry by means of the reference voltage, and the actual value of the physical parameter measured by the sensor element, the signal adapting circuitry will process the signal from the sensor element such that an adapted signal in accordance with the standard expected by the monitor may be optically sent back to the external device.

The transceiver unit is connected to the optical connector link that in turn is connected to the communication unit.

The optical connector link comprises a first communication means electrically connected to the transceiver unit to handle the communication to and from the transceiver unit, i.e. to convert an electrical signal from the transceiver unit to an optical signal and vice versa.

The optical connector link also comprises a second communication means electrically connected to the communication unit to handle the communication to and from the communication unit, i.e. to convert an optical signal from the transceiver unit to an electrical signal and vice versa.

The first communication means is energized by the energy means arranged in the transceiver unit.

The optical connector link is realized by at least one commercially available optocoupler, e.g. a high speed optocoupler by Hewlett-Packard having the product number 6N137, HCPL-26XX/06XX/4661 or HCNW137/26X1 that are optically coupled gates that combine a GaAsP light emitting diode and an integrated high gain photo detector.

As mentioned above also an analogue optical transmission may be used. Examples of available analogue optocouplers are e.g. 6N135, HCPL-0500 and CNW135 by Agilent Technologies. The necessary changes of the circuitry when using this type of optocouplers are obvious to a person skilled in the art.

When choosing type of optocoupler, irrespectively if it is a digital or analogue, the energy consumption of the optocoupler is an important parameter to consider.

The optocoupler ensures that no galvanic connection between the distal part and the proximal part of the measurement system is present.

According to a first embodiment the communication is a one-way communication from the transceiver unit (and the sensor) to the communication unit (and external device). In this embodiment the light emitting diode is arranged at the side facing the transceiver unit and the photo detector faces the communication unit.

According to a second embodiment of the invention the communication is a both-way communication, and in that case two optocouplers are arranged enabling communication in both directions.

For both embodiment more than one optocoupler may be arranged in either direction to provide redundancy for the optical communication link.

When the sensor wire has been inserted into the transceiver unit and the communication unit is connected to the external device the system is ready for use.

By e.g. pressing the activation button on, or by activating the transceiver in another way, the transceiver unit it is activated and will then try to establish an optical connection with the communication unit via the optical connector link. This is preferably performed by a conventional handshake procedure in order to identify the transceiver unit. The system is now ready to receive measured sensor data.

The sensor values is preferably A/D converted and supplied to the optical communication link as a pulse train.

The programmable sensor conditioning means is preferably implemented by means of a PGA309 programmable analog sensor conditioner. The PGA309 is particularly designed for resistive bridge sensor applications and contains three main gain blocks for scaling differential input bridge sensor signals. Hence, as discussed in the above, a signal representing the measured physiological variable may be adapted such that a signal in a format expected by the monitor is provided. This signal format is determined by the reference voltage supplied to the sensor signal adapting circuitry and the actual value of the signal measured by the sensor. The PGA309 can be configured for use with an internal or external voltage reference. According to the present invention, an internal reference voltage of e.g. +2.5V is supplied to the PGA309 from the energy means.

Thus, the conditioner means generates an analog output voltage signal related to the sensor signal such that the measured physiological variable, i.e. the pressure, may be retrieved by the external device.

Since each sensor element is an individual item with its own characteristics, each sensor assembly comprises a calibration means, preferably an electrically erasable programmable read-only memory (EEPROM) which contains individual calibration data obtained during calibration of the sensor element performed for each individual sensor wire assembly. The calibration is performed in connection with manufacture of the sensor wire. Calibration data takes into account parameters such as voltage offsets and temperature drift, etc.

The bridge sensor is preferably energized from the PGA309 via an excitation voltage $V_{EXC}$, generated by the PGA309 circuit, that in turn is energized by the energy source. As an alternative the sensor may be energized from a separate energy source, e.g. a battery or a capacitor means, arranged in the transceiver unit.

For a given excitation voltage $V_{EXC}$, e.g. generated by the PGA309 circuit, the output voltage ($V_{IN1}$-$V_{IN2}$) of the bridge is a voltage proportional to the physiological condition, e.g. pressure, applied to the sensor. Hence, the sensor output voltage ($V_{IN1}$-$V_{IN2}$) (sensor signal in FIG. 4) of the bridge is proportional to the e.g. pressure applied to the sensor, which for a given pressure will vary with the applied excitation voltage. This sensor output voltage is preferably compensated for temperature variation at the site of the sensor and is applied to the PGA309 circuit. The PGA309 circuit also includes gain blocks for adjusting the output signal from that circuit and used in addition to the output amplifying means mentioned above.

According to another preferred embodiment a processing means, preferably a microprocessor (e.g. a PIC16C770 or a nRF24E1, shown with dashed lines in FIG. 4) may further be employed to process and adapt the analog output voltage $V_{OUT}$ of the conditioned sensor, which output voltage is supplied via the PGA309 programmable analog sensor conditioner. The analog output signal from the PGA309 circuit is A/D-converted prior it is applied to the processing means. To adapt the sensor signal to the BP22 signal standard, it may be necessary to process the sensor signal further before it is applied to the physiology monitor. For instance a multiplying digital-analog converter (DAC) which possibly is comprised in the processing means is supplied with digital data (e.g. a 12-bit word) representing the signal measured by the sensor element and the reference voltage. The resulting product is sent via the optical communication link and communication unit to the external device and is proportional to the measured sensor signal and the reference voltage.

Figure 6:
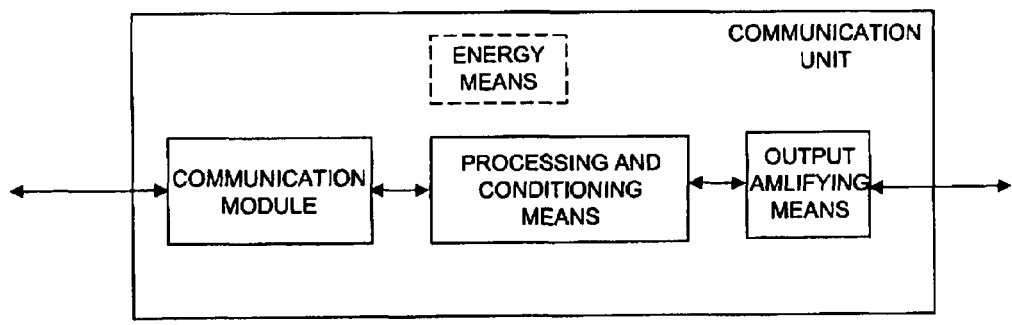
FIG. 6 shows a block diagram schematically illustrating a communication unit according to an alternative embodiment of the present invention.

In the preferred embodiment that has been described herein the adaptation of the sensor signal to the standard, e.g. BP22 signal standard, is performed in the transceiver unit, and in particular in the sensor signal adapting circuitry. However, this adaptation, in its entirety or only in parts, may, as an alternative, instead be performed by a corresponding circuitry arranged in the communication unit. This embodiment is schematically illustrated in FIG. 6. The transmitted sensor values would then be in the form of "raw" measured data that would be conditioned by a processing and conditioning means in the communication unit in order to be in a correct format to be supplied to the external system according to a prescribed standard format.

The transceiver unit, the optical communication link and the communication unit may preferably be arranged within a common enclosure, e.g. made from a plastic material, and an electrical wire connection connects the communication unit to the external device.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A measurement system comprising:
   a sensor wire provided, at its distal end, with a physiological condition sensor configured to measure a physiological condition inside a patient, and to provide measured data to an external device,
   a transceiver unit configured to be connected to a proximal end of the sensor wire,
   a communication unit connected with the external device,
   wherein said transceiver unit is configured to communicate, by a communication signal, with said communication unit, to transfer measured data to the external device, wherein the communication signal, including the measured data, is generated by the transceiver unit and is transferred as an output signal,
   wherein said communication unit is configured to be connected to a standard input/output connector of the external device and to communicate with the external device in accordance with an established standard, or in accordance with relevant parts of an established standard, and
   a physical optical communication link arranged between said transceiver unit and said communication unit,
   wherein said communication signal is an optical signal transferred by said optical communication link, and that said transceiver unit comprises an energy device configured to energize said sensor, said transceiver unit and a distal part of said optical communication link,
   wherein said transceiver unit comprises a sensor signal adapting circuitry configured to filter, process, and format the signal received from the sensor wire,
   wherein said sensor signal adapting circuitry comprises a programmable sensor conditioning device, a calibration unit, the energy device, and an output amplifying unit.

2. A measurement system according to claim 1, wherein said optical communication link comprises a first communication device configured to be electrically connected to the transceiver unit to handle the communication to and from the transceiver unit, to convert an electrical signal from the transceiver unit to an optical signal and vice versa.

3. A measurement system according to claim 2, wherein the optical communication link further comprises a second communication device configured to be electrically connected to the communication unit to handle the communication to and from the communication unit, to convert an optical signal to an electrical signal and vice versa.

4. A measurement system according to claim 2, wherein said energy device in the transceiver unit is configured to energize the first communication device of the optical communication link.

5. A measurement system according to claim 3, wherein the second communication device of the optical communication link is energized by the communication unit.

6. A measurement system according to claim 1, wherein the measurement system is configured such that a data stream is in the form of data packets.

7. A measurement system according to claim 1, wherein said transceiver unit and communication unit are provided with a device configured to perform bi-directional communication via said optical communication link.

8. A measurement system according to claim 1, wherein said communication signal is an infrared signal.

9. A measurement system according to claim 1, wherein said optical communication link is an optocoupler including a light emitting diode and an integrated high gain photo detector.

10. A measurement system according to claim 1, wherein the transceiver unit is activated and initiated by an activation device.

11. A measurement system according to claim 10, wherein said activation device is an activation button arranged on said unit.

12. A measurement system according to claim 1, wherein said transceiver unit comprises a female connector comprising an insulating hollow housing containing a predetermined number of hollow contact surfaces to make contact with the conductive surfaces of a male connector of the sensor wire.

13. A measurement system according to claim 12, wherein at a distal end of the female connector, a fastening device configured to secure the male connector in the female connector is provided.

14. A measurement system according to claim 13, wherein said transceiver unit is provided with a guiding device configured to guide the sensor wire during insertion into a patient.

15. A measurement system according to claim 12, wherein said transceiver unit is provided with a guiding device configured to guide the sensor wire during insertion into a patient.

16. A measurement system according to claim 1, wherein said programmable sensor conditioning device is a PGA309 programmable analog sensor conditioner.

17. A measurement system according to claim 1, wherein said energy device is a battery or a capacitor.

18. A measurement system according to claim 1, wherein the communication unit is configured adapted to receive sensor values in the form of "raw" measured data and to apply said data to a processing and conditioning device to process and condition the data to be supplied to the external device according to a prescribed standard format.

19. A measurement system according to claim 1, wherein said sensor is a pressure sensor.

20. A measurement system according to claim 19, wherein said pressure sensor is a piezoresistive, piezocapacitive, piezoelectric sensor or an optical sensor.

21. A measurement system according to claim 1, wherein said sensor is a temperature sensor.

22. A measurement system according to claim 1, wherein said sensor is a flow sensor.

23. The measurement system according to claim 1, wherein the established standard is BP22 or USB.

24. The measurement system according to claim 1, wherein the optical communication link is the only link between the transceiver unit and the communication unit.

25. A measurement system comprising:
a sensor wire provided, at its distal end, with a physiological condition sensor configured to measure a physiological condition inside a patient, and to provide measured data to an external device,
a transceiver unit configured to be connected to a proximal end of the sensor wire,
a communication unit connected with the external device,
wherein said transceiver unit is configured to communicate, by a communication signal, with said communication unit, to transfer measured data to the external device, wherein the communication signal, including the measured data, is generated by the transceiver unit and is transferred as an output signal,
wherein said communication unit is configured to be connected to a standard input/output connector of the external device and to communicate with the external device in accordance with an established standard, or in accordance with relevant parts of an established standard, and
a physical optical communication link arranged between said transceiver unit and said communication unit,
wherein said communication signal is an optical signal transferred by said optical communication link, and said transceiver unit comprises an energy device adapted to energize said sensor, said transceiver unit and a distal part of said optical communication link,
wherein the transceiver unit is activated and initiated by an activation device,
wherein said activation device is configured to activate and initiate the unit when electrical connections are established between corresponding electrical contact surfaces of female and male connectors of said transceiver unit and the proximal end of the sensor wire, respectively.

26. A measurement system comprising:
a sensor wire provided, at its distal end, with a physiological condition sensor configured to measure a physiological condition inside a patient, and to provide measured data to an external device,
a transceiver unit configured to be connected to a proximal end of the sensor wire,
a communication unit connected with the external device,
wherein said transceiver unit is configured to communicate, by a communication signal, with said communication unit, to transfer measured data to the external device, wherein the communication signal, including the measured data, is generated by the transceiver unit and is transferred as an output signal,
wherein said communication unit is configured to be connected to a standard input/output connector of the external device and to communicate with the external device in accordance with an established standard, or in accordance with relevant parts of an established standard, and
a physical optical communication link arranged between said transceiver unit and said communication unit,
wherein said communication signal is an optical signal transferred by said optical communication link, and said transceiver unit comprises an energy device adapted to energize said sensor, said transceiver unit and a distal part of said optical communication link,
wherein the transceiver unit is activated and initiated by an activation device,
wherein said activation device is an activation button arranged on said unit,
wherein said activation device is configured to activate and initiate the unit when electrical connections are established between corresponding electrical contact surfaces of female and male connectors of said transceiver unit and the proximal end of the sensor wire, respectively.

* * * * *